United States Patent
Raiszadeh

(10) Patent No.: US 11,065,310 B2
(45) Date of Patent: Jul. 20, 2021

(54) COMPOSITIONS AND METHODS FOR THROMBOEMBOLISM DISSOLUTION

(71) Applicant: NattoCat, LLC, Fairfax Station, VA (US)

(72) Inventor: Michelle Monier Raiszadeh, Fairfax Station, VA (US)

(73) Assignee: NATTOCAT, LLC, Fairfax Station, VA (US)

( * ) Notice: Subject to any disclaimer, the term of this patent is extended or adjusted under 35 U.S.C. 154(b) by 108 days.

(21) Appl. No.: 16/304,769

(22) PCT Filed: May 26, 2017

(86) PCT No.: PCT/US2017/034759
§ 371 (c)(1),
(2) Date: Nov. 27, 2018

(87) PCT Pub. No.: WO2017/205790
PCT Pub. Date: Nov. 30, 2017

(65) Prior Publication Data
US 2020/0254071 A1     Aug. 13, 2020

Related U.S. Application Data

(60) Provisional application No. 62/342,304, filed on May 27, 2016.

(51) Int. Cl.
| | | |
|---|---|---|
| *A61K 38/48* | (2006.01) | |
| *A61P 7/02* | (2006.01) | |
| *A61K 9/00* | (2006.01) | |
| *A61K 9/28* | (2006.01) | |
| *A61K 31/7048* | (2006.01) | |
| *A61K 36/75* | (2006.01) | |

(52) U.S. Cl.
CPC .......... *A61K 38/482* (2013.01); *A61K 9/0053* (2013.01); *A61K 9/28* (2013.01); *A61K 31/7048* (2013.01); *A61P 7/02* (2018.01)

(58) Field of Classification Search
None
See application file for complete search history.

(56) References Cited

U.S. PATENT DOCUMENTS

| | | |
|---|---|---|
| 8,287,858 B2 | 10/2012 | Barron |
| 8,343,517 B1 | 1/2013 | Bezzek |
| 2004/0043015 A1 | 3/2004 | Moriyama et al. |
| 2004/0223962 A1 | 11/2004 | Riordan |
| 2006/0222641 A1 | 10/2006 | Riordan |
| 2008/0044398 A1 | 2/2008 | Kwon |
| 2008/0193973 A1 | 8/2008 | Chen et al. |
| 2009/0136648 A1 | 5/2009 | Moriyama et al. |
| 2013/0004564 A1 | 1/2013 | Tasiemski et al. |
| 2013/0004565 A1 | 1/2013 | Barron |

FOREIGN PATENT DOCUMENTS

| | | |
|---|---|---|
| CN | 1204250 C | 6/2005 |
| CN | 103923896 A | 7/2014 |
| CN | 103948915 A | 7/2014 |
| CN | 103238829 B | 8/2015 |
| JP | A-2016-504287 | 2/1916 |
| JP | A-2004-143138 | 5/2004 |
| JP | A-2005-120035 | 5/2005 |
| JP | 2005/220025 | 8/2005 |
| JP | B2-3881494 | 11/2006 |
| JP | B2-5715635 | 3/2015 |
| KR | 2001 0067732 | 7/2001 |
| KR | 2001-0067732 | 7/2001 |
| WO | WO 2008/019417 | 2/2008 |
| WO | WO 2014/079689 | 5/2014 |

OTHER PUBLICATIONS

Thesis Abstract, "Preparation and Antithrombotic Effect of Nattokinase Enteric-Coated Capsules," Liang Shuang (http://www.dissertationtopic.net/doc/428404) (2011).
Internet article, "Nattokinase," Natural Medicines Comprehensive Database (2015).
Internet article, "The Superfood-Based Solution to Superior Heart Health," Vitamin Research Products (http://www.vrp.co.za/Public/ViewArticle.aspx?ArticleID=156) (2011).
Internet article, "Nattokinase," Examine.com (https://examine.com/supplements/nattokinase) (2016).
Internet article, "Hypertrophic Cardiomyopathy in Cats Explained," Pets4Homes (2016).
Extended European Search Report for PCT/US2017/034759 dated Nov. 20, 2019.
Law, D. et al. "Stabilization and Target Delivery of Nattokinase Using Compression Coating", Drug Development and Industrial Pharmacy, vol. 33, 2007, pp. 495-503, XP055093338.
Milner, M. et al., "Natto and Its Active Ingredient Nattokinase", Alternative and Complementary Therapies, Jun. 2002, pp. 157-164, XP009118951.
International Search Report for PCT/US2017/034759 dated Aug. 15, 2017, 3 pages.
Written Opinion of the ISA for PCT/US2017/034759 dated Aug. 15, 2017, 8 pages.

*Primary Examiner* — Suzanne M Noakes
*Assistant Examiner* — Jae W Lee
(74) *Attorney, Agent, or Firm* — Joshua B. Brady; Nixon & Vanderhye, P.C.

(57) ABSTRACT

Disclosed herein are novel thrombolytic formula for safe and effective treatment of blood clots. In clinical trials, cats of various breeds and ages presented partial or full paralysis of one or more limbs, due to arterial thromboembolism (ATE). Average treatment ranged from 3 days to 2 weeks, depending on the clot size and time elapsed since clot was dislodged from the subject's heart. These are significant findings considering the lack of treatment options available in veterinary medicine for cats with HCM and ATE. Veterinarians often euthanize cats presenting ATE, as no safe and effective thrombolytic agent is currently available for veterinary use. Previous thrombolytics were shown to have an average mortality rate of 60% due to reperfusion injury and hemorrhaging. The disclosed formula, on the other hand, overcomes these shortcomings.

13 Claims, No Drawings

COMPOSITIONS AND METHODS FOR THROMBOEMBOLISM DISSOLUTION

RELATED APPLICATION

This application claims the benefit of U.S. Provisional Patent Application No. 62/342,304, which is incorporated by reference in its entirety.

FIELD OF THE INVENTION

The present invention relates to compositions and methods for dissolving thromboembolisms, and in particular thromboembolisms in felines.

BACKGROUND—INTRODUCTION

The most common form of heart disease in cats, hypertrophic cardiomyopathy (HCM) is a progressive condition in which there is no known cure. Approximately 15% of all cats have hypertrophic cardiomyopathy. Cats of either sex can be affected, although males are typically affected more than females. The disease has been reported in cats ranging in age from 3 months to 20 years.

In HCM, cardiac muscle tissue is replaced with scar tissue. Due to scar tissue buildup, HCM causes thickening of the papillary muscles that anchor the mitral valve and the walls of the left ventricle. The left ventricle is the heart chamber responsible for pumping blood out through the aorta. HCM affects the ventricle's ability to pump blood through the heart and causes the left atrium to become enlarged from blood backing up. Though cats with HCM are given a guarded prognosis, there are several potential outcomes for cats with HCM. Many cats respond well to medical therapy and remain symptom-free for years. Some cats develop fatal heart arrhythmias and die suddenly. In some cats, the disease progresses steadily, ultimately leading to congestive heart failure. These severely affected cats have difficulty breathing due to the accumulation of fluid in or around the lungs. Furthermore, a significant number of cats with HCM develop arterial thromboembolism (ATE). These blood clots are one of the most serious complications associated with hypertrophic cardiomyopathy, and are one of the most common causes of hind limb paralysis in felines that almost always leads to euthanasia. ATE occurs in 20 to 40 percent of cats with cardiomyopathy.

The blood clots develop in the left atrium or the left ventricle. Due to the ventricle's inability to pump blood through the heart and resulting blood backup in the left atrium, blood tends to pool and stagnate in the left atrium, the top heart chamber. Where blood flow is stagnant, clots tend to form. Inevitably, the clot or a fragment of it breaks loose and enters the circulation. Small clots may go undetected until they obstruct blood flow. The most common blockage point is in the lower abdomen where the aorta, the main blood vessel leaving the heart, forms two branches going to the back legs. This spot is known as the saddle, and it is common for the blood clot to come to rest at the top of that point, leading to the term saddle thrombus.

Clinically this presents as a cat with complete loss of function or paralysis in one or both hindlimbs. The rear limbs are cold and muscles and nerves swell due to lack of oxygen and nutrients. The cat is in severe pain derived from the exaggerated inflammatory response to the embolus at the point of impact, and the inflammatory mediators released generally have a vasoconstrictor effect further exacerbating the problem. Ninety percent of cats with ATE have a pre-existing heart problem such as HCM. A large enough clot forms a classic saddle thrombus, although smaller fragments have been known to make it farther downstream to the intestines, brain, renal artery or ovarian/testicular arteries as they exit the abdominal aorta. Blockage of the renal artery can lead to acute renal failure. Emboli may also block circulation to a forelimb, leading to partial or complete forelimb paralysis.

The signs of ATE come on suddenly and may include:
Dragging of one or both hind legs.
Difficulty breathing.
Crying or screaming.
Panting or open-mouthed breathing.
Lack of pulses in one or both hind legs.
Rear legs that are cool to the touch.
Leg muscles that are hard and extremely painful.
Paw pads and nail beds that appear cyanotic (blue-tinged).
Heart murmur or arrhythmia.
Abnormal lung sounds.

Complete recovery is rare, as recurrences of ATE are common and most cats have serious progressive heart disease as the underlying cause. ATE or saddle thrombus is a serious and sometimes fatal complication of heart disease in cats. In addition, ATE usually strikes without warning; in fact, it may be the first and only sign of heart disease in some cases. ATE is an extremely serious and painful condition. Due to the uncertain outlook and the possibility of underlying heart disease, most pet parents elect humane euthanasia rather than treatment.

Other causes of clot formation in the cat include hyperthyroidism and certain cancers, especially lung cancer.

Some breeds are predisposed to HCM. In recent years, direct DNA tests have been developed for Ragdolls and Maine Coons that allow breeders and owners to identify those that carry the gene mutation for HCM. Even with the genetic tests, the complexity of HCM can be baffling. Cats that test negative may still develop the disease, and different forms of HCM are believed to occur in different breeds and even in individual cats.

While there is no cure for HCM, early detection and regular echocardiograms are key to trying to ward off life-threatening problems. Early signs may include a murmur or even heart failure. Unfortunately, death may occur without any other signs present, making the disease a difficult and often deadly one. While medication is commonly given to cats with HCM that have no clinical signs, no medication has been shown to be helpful at this stage and it has been shown that an ACE inhibitor is not beneficial until heart failure is present (at which time a diuretic such as Furosemide (Lasix) is most beneficial). Diltiazem generally produces no demonstrable benefit. Atenolol is commonly administered when systolic anterior motion of the mitral valve is present.

Veterinary drugs previously available on the market that have the potential to dissolve a thrombus or embolus are tissue-plasminogen activator (tPA) and streptokinase. TPA is very expensive with one 50 mg vial costing over $1000. Studies using this drug in cats are scarce. In one study, about two-thirds of cats given this drug had perfusion restored to their limbs. Streptokinase is less expensive. A study of 46 cats with ATE that were treated with streptokinase showed about half of the cats had their pulses restored, and 30% had motor function returned to their limbs within 24 hours.

The side effects of treating cats with streptokinase or tPA make their use questionable. When cats are treated with these agents, they become susceptible to "reperfusion injury" as blood flow is suddenly restored to the limbs.

Electrolyte disturbances such as hyperkalemia (excessively high potassium levels) and metabolic acidosis can result, with direct consequences. In one report of using tPA to treat cats with ATE, 70% of fatal complications were due to metabolic acidosis and hyperkalemia. Hemorrhage can be another adverse side effect, since these drugs are designed to dissolve clots. These drugs must also be administered within 2 hours to be effective.

The risk of reperfusion injury, hemorrhage, the significant cost of the drugs, and the lack of evidence of improved outcome in cats treated with these particular thrombolytic agents makes their use questionable, and many practitioners remain reluctant to administer this form of therapy. Furthermore, neither tPA or streptokinase are used for the prevention of clot formation in at risk felines.

Though there is no known cure for HCM, veterinarians often prescribe medications to treat signs of the disease. These include:
  eta blockers, which may help slow the heart rate and decrease the severity of abnormalities that occur secondary to HCM.
  Calcium channel blockers, which may improve heart function by reducing heart rate and myocardial oxygen consumption.
  ACE (angiotensin-converting-enzyme) inhibitors, which help decrease scarring and thickening of the heart muscle to slow or prevent disease progression.
  Diuretics, which are effective in treating pulmonary edema and pleural effusion.

While streptokinase and tissue-plasminogen activators have been discontinued in treating ATE, blood thinning medications are often prescribed for prevention of thromboembolisms. Currently, no prescription blood thinning agents are available that guarantee prevention of blood clot formation in felines. Furthermore, blood thinning agents available on the market do not exhibit characteristics of a thrombolytic agent. Typically, low dose of aspirin may be prescribed for prevention of clot formation in felines. Aspirin, however, is extremely toxic to cats and should only be prescribed and administered by a veterinary surgeon. Plavix (Clopidogrel) is also another widely used drug that may or may not prevent clot formation in HCM cats. So, currently, the standard treatment for clots has been administration of blood thinners for prevention of new clots, pain management and heart failure treatment, if signs are present. Unfortunately, less than 40 percent of cats with ATE survive and the recurrence of ATE is highly likely in these cats, often leading to euthanasia.

In addition, contemporary thrombolytics available in supplement form have lacked potency, primarily due to high rates of active ingredient dissolution in stomach acids. This prevents entry of thrombolytics into the small intestine where it could be absorbed into the bloodstream in order to be effective in clot dissolution and prevention.

BRIEF SUMMARY

An independent research study demonstrated that embodiments of the enzymatic formula described herein may be used in novel, safe, affordable and effective methods of dissolving and preventing blood clots in cats suffering from ATE. This formula has been shown to safely and effectively dissolve clots in cats over two weeks since the clot was first dislodged from the heart. Unlike tPA or streptokinase, the formula described herein does not need to be administered immediately or within 2 hours of ATE to fully dissolve clots and restore circulation to affected areas.

Furthermore, there were no cases in the research study that resulted in adverse side effects, such as, for example, hemorrhaging and reperfusion injury from the administration of embodiments of the enzymatic formula for the treatment of thromboembolisms. This is in combination with diuretics such as Furosemide for cats with congestive heart failure and other heart related medications for HCM. In the research study, embodiments of the enzymatic formula were administered without any other blood thinning or thrombolytic agents to prevent complications, such as internal bleeding and bruising. However, no other thrombolytic or blood thinning agents were necessary in combination with this formula to effectively dissolve blood clots before tissue necrosis set in.

Embodiments of the enzymatic formula include nattokinase and rutin bioflavonoid. In some embodiments, the nattokinase may be present in a single dose at approximately 37.5 mg/750 fibrinolytic units, although the concentration may vary in other embodiments. In some embodiments, the rutin bioflavonoid may be present in a single dose at approximately 50 mg, although the concentration may vary in other embodiments. Some embodiments may be in the form of a tablet, the tablet having nattokinase at approximately 37.5 mg/750 fibrinolytic units, and rutin bioflavonoid at approximately 50 mg.

Some embodiments may also include an enteric coating to reduce dissolution of the formula in the gastric environment. In some embodiments, the enteric coating may be a polymer barrier such as, for example, a methacrylic acid copolymer and triethyl citrate coating. For example, some embodiments may be in the form of a tablet having an enteric coating. Some embodiments may take the form of a capsule, pill, or gelcap with an enteric coating. Liquid embodiments are contemplated, however, it is expected that the lack of an enteric coating may reduce the efficacy of the active ingredients when delivered as a liquid medium. It is also contemplated that some embodiments will comprise an injectable liquid form that can be administered directly into the bloodstream, and in such embodiments, an enteric coating would not be required.

Treatment methods may include oral administration of a dose of the enzymatic formula. For cats weighing between about 7 lbs to about 30 lbs, a treatment dose of about 1,125 mg/day is recommended for up to two weeks, or until the clot is fully dissolved. With about 562.5 mg administered in the morning, and about 562.5 mg administered approximately 12 hours later or at night. For cats in this weight range, a maintenance dose of about 75 mg/day for cats with a form of less severe HCM is recommended for their lifetime, or as long as they are at risk for clots.

In maintenance embodiments, about 37.5 mg may be administered in the morning, and about 37.5 mg may be administered at night or about 12 hours after the initial dose. For cats with a more severe form of HCM in this weight range, a maintenance dose of 150 mg/day to 225 mg/day is recommended for their lifetime, or as long as they are at risk for clots. In maintenance embodiments, about 75 mg to 112.5 mg may be administered in the morning, and about 75 mg to 112.5 mg may be administered at night or about 12 hours after the initial dose. Alternatively, doses can be given throughout the day rather than only in the morning and night, though it is presently recommended that dosing not exceed 1,125 mg/day for subjects in this weight range. For cats weighing less than 7 lbs, a treatment dose of about 750 mg/day is recommended based on present data. For cats weighing less than 7 lbs, a maintenance dose of about 75 mg/day is still recommended, with about 37.5 mg administered twice a day, approximately 12 hours apart.

In some embodiments, a treatment regimen includes orally administering about 10-30 tablets initially, and then orally administering about 10-30 tablets after approximately 12 hours after the initial administration, each tablet having nattokinase at approximately 37.5 mg/750 fibrinolytic units, and rutin bioflavonoid at approximately 50 mg. In some embodiments, the initial and/or subsequent treatments may include administering about 10-20 tablets, and in other embodiments about 20-30 tablets. For example, 15 tablets may be orally administered at time 0 hours, and another 15 tablets may be orally administered at time 12 hours. It should be appreciated that for some patients, particularly smaller patients, fewer than 10 tablets may be appropriate. For example, some patients may require 6-8 tablets initially, and 6-8 tablets in subsequent doses. Those of skill in the art will recognize that the species and body mass, among other factors relating to the particular patient, may require larger or smaller doses.

In some embodiments, a maintenance regimen includes orally administering a more concentrated form of the tablet at 112.5 mg/2,250 fibrinolytic units and rutin bioflavonoid at approximately 150 mg for cats with a more severe form of HCM. This would be done twice a day and 12 hours apart.

In some embodiments, a treatment regimen includes orally administering a more concentrated form of the tablet at 225 mg/4,500 fibrinolytic units and rutin bioflavonoid at approximately 300 mg for cats 5 times per day for every 12 hours.

Although embodiments disclosed herein, and the clinical trial data presented herein, relate to feline patients, it should be appreciated that embodiments of the present approach may be effective for use in other animals, including, for example, humans and non-human species such as dogs, horses, and other non-human animals for clot dissolution.

DESCRIPTION

The present disclosure relates to compositions and methods for dissolving thromboembolisms, and in particular thromboembolisms in felines. Embodiments of the enzymatic formula include nattokinase and rutin bioflavonoid. In some embodiments, the nattokinase may be present in a single dose at approximately 37.5 mg/750 fibrinolytic units, although the concentration may vary in other embodiments. In some embodiments, the rutin bioflavonoid may be present in a single dose at approximately 50 mg, although the concentration may vary in other embodiments. Some embodiments may be in the form of a tablet, the tablet having nattokinase at approximately 37.5 mg/750 fibrinolytic units, and rutin bioflavonoid at approximately 50 mg. It should be appreciated, though, that the dose may be larger or smaller, depending on the patient.

Some embodiments may also include an enteric coating to reduce dissolution of the formula in the gastric environment. In some embodiments, the enteric coating may be a polymer barrier such as, for example, a methacrylic acid copolymer and triethyl citrate coating. For example, some embodiments may be in the form of a tablet having an enteric coating.

Treatment methods may include oral administration of a dose of the enzymatic formula. In some embodiments, a treatment regimen includes orally administering 10-30 tablets initially, and then orally administering 10-30 tablets after approximately 12 hours after the initial administration, each tablet having nattokinase at approximately 37.5 mg/750 fibrinolytic units, and rutin bioflavonoid at approximately 50 mg. For example, 15 tablets may be orally administered at time 0 hours, and another 15 tablets may be orally administered at time 12 hours.

In a preferred embodiment, the thrombolytic enzymatic formula includes the following active ingredients: nattokinase (37.5 mg/750 fibrinolytic units) and rutin bioflavonoid (50 mg). Nattokinase is a naturally occurring proteolytic enzyme derived from natto, a traditional Japanese food produced from the fermentation of soybeans with Bacillus subtilis natto. Bacillus subtilis are rod-shaped, gram-positive and catalase-positive bacteria. Nattokinase is an enzyme that digests fibrin both directly and indirectly. Indirectly, it activates pro-urokinase and tissue plasminogen activator (t-PA), supporting the fibrinolytic activity of plasmin. These combined actions promote healthy platelet function, circulation and blood flow. In its purified form, the enzyme shows its optimum conditions at 37° C. and a pH of 7. The enzyme activity gradually declines at temperatures beyond 70° C. The enzyme may contribute to the regular healthy function of the heart and cardiovascular system by maintaining proper blood flow, thinning the blood and preventing blood clots. For this reason, nattokinase may hydrolyze fibrin in blood clots.

The inventor confirmed that oral administration of nattokinase produced a mild and frequent enhancement of the fibrinolytic activity in the plasma and the production of tissue plasminogen activator. In a Japanese study, nattokinase capsules had been administered orally to dogs that received artificially induced thrombosis, and lysis of the thrombi was observed by angiography. The enzyme was already active in circulation prior to the clot being induced, so this does not demonstrate the enzymes efficacy to dissolve clots dislodged over a period of days or weeks. Regardless, results obtained from this Japanese study suggest that nattokinase may represent a possible drug for use not only in the treatment of embolism but also in the prevention of the disease. There are no known studies that examine the efficacy of nattokinase as a thrombolytic agent in cats.

Rutin, also called rutoside, quercetin-3-O-rutinoside and sophorin, is the glycoside between the flavonolquercetin and the disaccharide rutinose ($\alpha$-L-rhamnopyranosyl-(1→6))-$\beta$-D-glucopyranose). Rutin is one of the phenolic compounds found in the invasive plant species *Carpobrotus edulis* and contributes to the antibacterial properties of the plant. Its name comes from the name of *Ruta graveolens*, a plant that also contains rutin. Rutin is a citrus flavonoid glycoside found in many plants including buckwheat, the leaves and petioles of *Rheum* species, and asparagus. Tartary buckwheat seeds have been found to contain more rutin (about 0.8-1.7% dry weight) than common buckwheat seeds (0.01% dry weight). Rutin is also found in the fruit of the fava d'anta tree (from Brazil), fruits and flowers of the pagoda tree, fruits and fruit rinds (especially the citrus fruits orange, grapefruit, lemon, and lime) and apple; berries such as mulberry, ash tree fruits, aronia berries and cranberries.

In the fava d'anta tree, the synthesis is done via a rutin synthase activity. Rutin is one of the primary flavonols found in 'clingstone' peaches. It is also found in green tea infusions. Rutin inhibits platelet aggregation, as well as decreases capillary permeability, making the blood thinner and improving circulation. Recent studies show rutin could help prevent blood clots so could be used to treat patients at risk of heart attacks and strokes. Rutin may also have a veterinary use in the management of chylothorax in dogs and cats. In other words, rutin may potentially help decrease fluid buildup in the lungs during congestive heart failure.

Along with blood clots, congestive heart failure is a common occurrence in cats with hypertrophic cardiomyopathy (HCM).

Since both nattokinase and rutin have demonstrated thrombolytic activity based on data collected in the inventor's private research study, the inventor's private research study investigated combining the two agents to make a more powerful thrombolytic pharmaceutical. However, both agents can be dissolved in stomach acids, rendering certain dosage forms nearly useless as thrombolytic agents. This may explain why the potency of previous oral thrombolytics is decreased in comparison to injected thrombolytic agents. Enteric coatings reduce the active ingredients' rate of digestion in stomach acids, leading to enhanced efficacy of the active ingredient(s).

To ensure the efficacy of these two thrombolytic agents, an enteric coating is appropriate for some orally administered embodiments. The enteric coating allows the nattokinase and rutin bioflavonoid to travel through the acidic environment of the stomach without being dissolved. Nattokinase and rutin can then be absorbed into the bloodstream or circulation via the small intestine. Once absorbed, nattokinase remains active in the bloodstream for approximately 12 hours. In one embodiment, the enteric coating is composed of methacrylic acid copolymer and triethyl citrate. Additional ingredients may include, for example, arabinoglactan, microcrystalline cellulose, maltodextrin, stearic acid, croscarmellose sodium, silicon dioxide. During this clinical trial, participants were not on any other thrombolytic or fibrinolytic (blood thinning) agents.

During the inventor's research study, cats presented signs of ATE including hindlimb paralysis, low or absent pulse in affected limb(s), cold and darkened paw pads from low or no blood supply in affected limb(s). Hardened tissue, raw skin and hair loss on affected limb(s). Cats exhibited pain or numbness in affected limb(s) and some cats showed signs of congestive heart failure in the form of coughing and other symptoms directly related to pleural effusion. These cats were immediately put on diuretics including Furosemide (Lasix) to drain fluid from their lungs. Once the cats were stable, 15 tablets of an embodiment of the enzymatic formula were administered orally in the morning. 12 hours later, 15 tablets of an embodiment of the enzymatic formula were administered orally.

For the embodiments used in the inventor's research study, it was preferred to reduce the likelihood that a subject would chew up a tablet, because the enteric coating had to remain intact for maximum efficacy. Additionally, the inventor's research study indicated that stress on the subject may be reduced by breaking up the treatment dose over the course of a day. For example, with subjects between about 7 pounds and about 21 pounds in bodyweight, dividing the initial dosage of about 1,125 mg/day into two doses, approximately 12 hours apart, appears sufficient to minimize stress on the subject and also maintain an adequately high concentration of effective ingredients to break down the clot.

Of the 46 cats in the inventor's research study, 2 had dislodged clots from their heart and into circulation within an hour to 5 hours of treatment. The rest had dislodged clots from their heart within 1 day to 2 weeks of treatment. In all cases, circulation and mobility returned, with no adverse reactions to the formula embodiment. One cat had not received treatment until 2 weeks after the onset of ATE. This cat regained full circulation to his hindlimbs, but lost 1 digit on his right hindlimb, because necrosis had set into that tissue prior to treatment. After a full 3 week treatment of 15 tablets in the morning and 15 tablets at night, this cat regained function of his affected hindlimbs and was able to walk again. Damaged peripheral tissue had also regenerated during treatment.

The recommended treatment dose for 1 blood clot is approximately 10-30 tablets, and in embodiments about 15 tablets, every 12 hours, and for the earlier of approximately 2 weeks or until full circulation and mobility has returned to affected limbs. If more than one clot is present, the treatment dose may be extended, e.g., to about 3 weeks instead of about 2 weeks. In some embodiments, the daily treatment dose of 30 tablet/day does not need to be increased for the treatment dose. For kittens or cats weighing less than 7 lbs, 15 tablets/day may be administered to determine whether the lower concentration is adequate for the subject. In some embodiments, for kittens or cats weighing less than 7 lbs, the maintenance dose of 1 tablet in the morning and 1 tablet at night, may be effective and safe. Though it is difficult to determine if more than one clot is present, the treatment may continue past 2 weeks if multiple clots are suspected. Generally, treatment should continue until full mobility, color, and temperature have returned to affected limbs. This may mean the treatment may exceed 4 weeks, though in some embodiments it may be appropriate to lower the dosage to half of the treatment dosage after the third week. In some embodiments, after recovery and full dissolution of the thromboembolism, cats are placed on a maintenance dose of 1 tablet in the morning and 1 tablet at night, 12 hours apart. Generally, the treatment should be maintained as long as the subject is at risk of developing further blood clots. For some subjects, this may be for the life of the subject. In the private research study, the maintenance dose effectively prevented new clot formation in the hearts of cats with hypertrophic cardiomyopathy (HCM). Therefore, the disclosed treatment may be used to prevent blood clot formation in the heart.

In one embodiment, a method for treating thromboembolism in felines may take the form of:

Nattokinase Rutin Thrombolytic Treatment Dose: 2 week treatment. 15 tablets in the morning before meals and 15 tablets in the evening before meals every day until full circulation returns, wherein each tablet has nattokinase at approximately 37.5 mg/750 fibrinolytic units, and rutin bioflavonoid at approximately 50 mg. Each tablet may also include an enteric coating.

30 tablets per day=1,125 mg/day [of nattokinase, and 1,500 mg/day rutin bioflavonoid]

30 tablets×14 days=420 tablets for an average treatment of 1 clot

Total of 37.5 mg×420 tablets=15,750 mg [of nattokinase, and 21,000 mg rutin bioflavonoid] for 1 full treatment of 1 clot Nattokinase-Rutin Maintenance Dose (for prevention of clot formation): 2 tablets per day (1 tablet in the morning and 1 tablet before bedtime) given 12 hours apart 75 mg/day for daily maintenance dose Table 1 shows data for all 46 subjects in a private research study. Data includes subject number, age, gender, weight, date of treatment, location of blood clot, length of treatment and if clot formation occurred while subject was on maintenance dose.

TABLE 1

| Subject Number | Age (years) | Breed | Weight (lbs) | Gender | Location of Clot | Clot Dislodged from Heart | Length of Treatment | Treatment Dose (mg) | New Clot Formation While on Maintenance Dose |
|---|---|---|---|---|---|---|---|---|---|
| 1 | 3 | Domestic Shorthair Polydactyl | 12 | Male | Right Forelimb | 10 minutes | 20 minutes | 825 | No |
| 2 | 9 | Domestic Shorthair | 10 | Male | Both Hindlimbs | 3 days | 2 days | 2,250 | No |
| 3 | 18 | Domestic Shorthair | 13.5 | Male | Both Hindlimbs | 2 days | 5 days | 5,625 | No |
| 4 | 8 | Domestic Shorthair | 7 | Male | Both Hindlimbs | 2 days | 4 days | 4,500 | No |
| 5 | 10 | Domestic Shorthair | 11 | Male | Both Hindlimbs | 4 days | 1 week | 7,875 | No |
| 6 | 17 | Domestic Shorthair | 9.4 | Male | Both Hindlimbs | 5 days | 5 days | 5,625 | No |
| 7 | 14 | Domestic Shorthair | 9 | Male | Right Hindlimb | 3 days | 2 days | 2,250 | No |
| 8 | 12 | Domestic Shorthair | 12 | Male | Both Hindlimbs | 1 week | 3 days | 3,375 | No |
| 9 | 8 | Domestic Shorthair Tuxedo | 10 | Male | Right Hindlimb | 2 weeks | 6 days | 6,750 | No |
| 10 | 19 | Domestic Shorthair | 12 | Male | Both Hindlimbs | 1 day | 4 days | 4,500 | No |
| 11 | 9 | Domestic Shorthair | 13 | Male | Right Forelimb | 1 day | 2 days | 2,250 | No |
| 12 | 8 | Domestic Shorthair | 9 | Female | Both Hindlimbs | 1 week | 10 days | 1,875 | No |
| 13 | 12 | Domestic Shorthair | 11 | Male | Both Hindlimbs | 9 days | 2 weeks | 15,750 | No |
| 14 | 12 | Domestic Shorthair Tuxedo | 9 | Male | Both Hindlimbs | 3 days | 1 day | 1,125 | No |
| 15 | 9 | Domestic Shorthair | 8.5 | Female | Both Hindlimbs | 1 day | 9 days | 10,125 | No |
| 16 | 11 | Domestic Shorthair | 12 | Male | Left Forelimb | 2 days | 10 days | 11,250 | No |
| 17 | 9 | Siamese Himalayan | 12 | Male | Both Hindlimbs | 1 week | 5 days | 5,625 | No |
| 18 | 5 | Domestic Longhair | 8.5 | Male | Both Hindlimbs | 2 days | 3 days | 3,375 | No |
| 19 | 3 | Domestic Shorthair | 9.4 | Male | Both Hindlimbs | 4 days | 1 day | 1,125 | No |
| 20 | 9 | Domestic Shorthair | 8 | Male | Both Hindlimbs | 1 day | 8 days | 9,000 | No |
| 21 | 14 | Domestic Longhair | 21 | Male | Both Hindlimbs | 3 days | 5 days | 5,625 | No |
| 22 | 13 | Domestic Mediumhair | 16 | Male | Both Hindlimbs | 5 days | 5 days | 5,625 | No |
| 23 | 9 | Domestic Shorthair | 15.4 | Female | Right Hindlimb | 3 days | 1 week | 7,875 | No |
| 24 | 16 | Domestic Shorthair | 13 | Male | Partial Hindlimb | 3 weeks | 3 days | 3,375 | No |
| 25 | 11 | Domestic Shorthair | 14 | Female | Both Hindlimbs | 5 days | 4 days | 4,500 | No |
| 26 | 10 | Domestic Shorthair | 9 | Female | Both Hindlimbs | 3 days | 4 days | 4,500 | No |
| 27 | 13 | Domestic Shorthair | 11 | Male | Both Hindlimbs | 1 day | 3 days | 3,375 | No |
| 28 | 5 | Domestic Shorthair | 14 | Male | Both Hindlimbs | 2 days | 3 days | 3,375 | No |
| 29 | 4 | Domestic Shorthair | 15.4 | Male | Both Hindlimbs | 5 days | 2 weeks | 15,750 | No |
| 30 | 10 | Domestic Mediumhair | 10 | Male | Both Hindlimbs | 6 days | 1 week | 7,875 | No |
| 31 | 4 | Domestic Shorthair | 15 | Female | Both Hindlimbs | 1 week | 2 weeks | 15,750 | No |
| 32 | 2 | Domestic Shorthair | 7.5 | Female | Both Hindlimbs | 5 days | 4 days | 4,500 | No |
| 33 | 1 | Domestic Shorthair | 11 | Male | Left Hindlimb | 4 days | 3 days | 3,375 | No |
| 34 | 14 | Domestic Shorthair | 13 | Male | Both Hindlimbs | 4 days | 1 week | 7,875 | No |
| 35 | 4 | Domestic Shorthair | 12 | Male | Both Hindlimbs | 1 week | 2 weeks | 15,750 | No |

TABLE 1-continued

| Subject Number | Age (years) | Breed | Weight (lbs) | Gender | Location of Clot | Clot Dislodged from Heart | Length of Treatment | Treatment Dose (mg) | New Clot Formation While on Maintenance Dose |
|---|---|---|---|---|---|---|---|---|---|
| 36 | 14 | Maine Coon | 8.2 | Female | Left Forelimb | 4 days | 1 week | 7,875 | No |
| 37 | 10 | Domestic Shorthair | 9 | Female | Right Hindlimb | 6 days | 2 weeks | 15,750 | No |
| 38 | 12 | Persian | 12 | Male | Both Hindlimbs | 2 weeks | 2 weeks | 15,750 | No |
| 39 | 14 | Domestic Shorthair | 11 | Male | Both Hindlimbs | 2 weeks | 2.5 weeks | 19,125 | No |
| 40 | 9 | Domestic Shorthair | 16.8 | Female | Both Hindlimbs | 3 days | 4 days | 4,500 | No |
| 41 | 17 | Persian | 9 | Male | Both Hindlimbs | 1 week | 1 day | 1,125 | No |
| 42 | 16 | Domestic Shorthair | 14 | Male | Both Hindlimbs | 4 days | 2 weeks | 15,750 | No |
| 43 | 8 | Domestic Shorthair | 12 | Male | Left Hindlimb | 2 weeks | 2 weeks | 15,750 | No |
| 44 | 3 | Domestic Shorthair | 11 | Female | Both Hindlimbs | 4 days | 1 week | 7,875 | No |
| 45 | 1 | Domestic Shorthair | 12 | Male | Right Hindlimb | 1 week | 9 days | 10,125 | No |
| 46 | 9 | Bengal | 14.8 | Male | Both Hindlimbs | 8 days | 1 week | 7,875 | No |

Because blood clots are diagnosed or determined to exist through the following symptoms/observations, these factors were used to determine if they no longer existed, as well. Length of treatment was dependent on whether or not signs remained that a clot still existed. These factors or signs of a clot are: decreased mobility, partial paralysis or full paralysis of one or more limbs, decreased temperature in affected limbs, decreased color of paw pad in affected limbs. Unaffected limbs were used as a reference point to compare affected limbs. So, length of treatment was dependent on the length of time it took for the blood clot to be dissolved and these symptoms to no longer appear. With increased temperature, mobility, and the return of color to the cat's affected limb, it could be determined that the clot was in the process of being dissolved or was already dissolved. Stiffness from dehydration and lack of blood flow through affected tissue is also a symptom of a blood clot, so this can also be used to determine if the clot is still present and blocking circulation. Hence, when these symptoms subsided, the treatment dose could be changed to a maintenance dose.

Dosage in the clinical trial was determined in a similar way. The first cat in this study received the treatment only minutes after having a clot dislodged into circulation from his heart. The inventor initially administered 5 tablets, noticed no change, and administered 5 more, noticed no change, but once the inventor reached 15 tablets, she started to see a slight improvement. She could feel the temperature in his affected limbs increase and, after administering 15 more tablets within the next 10 minutes, the inventor could see a full recovery occur. Since the inventor did not want to risk internal bleeding by administering more than 30 tablets, she decided to cut off the treatment at this point. The inventor concluded 30 tablets was sufficient to dissolve one clot safely, and she decided to make this the cut off point, since it had shown to be an effective dose in other cats with various sized clots. The inventor still had no way to measure clot size, but can only assume they vary in size in each case.

Due to the preference for a high concentration of the nattokinase-rutin formula in order to effectively dissolve blood clots, the enzymatic formula is expected to have increased efficacy at high concentrations, e.g., as highly concentrated tablets. In embodiments used for the inventor's research study, each tablet contained about 37.5 mg of nattokinase and 50 mg of rutin, in tablet form having an enteric coating. Length of treatment would be reduced and the concentration would still be considered safe at 225 mg of nattokinase and 300 mg of rutin per tablet. This is based on the previous data where a 1 day treatment to dissolve ATE consisted of 1,125 mg nattokinase and 1,500 mg of rutin. Increasing the concentration of the current formula in tablet, capsule or gelcap form, would decrease the time it takes to dissolve clots and decrease the stress on the cat, owner and/or participating medical staff. It should be appreciated that alternative concentrations of each active ingredient, relative concentrations, and treatment regimens, other than those employed in connection with the clinical trial, may be employed without departing from the principles described herein.

The invention may be embodied in other specific forms without departing from the spirit or essential characteristics thereof. The present embodiments are therefore to be considered in all respects as illustrative and not restrictive, the scope of the invention being indicated by the claims of the application rather than by the description, and all changes which come within the meaning and range of equivalency of the claims are therefore intended to be embraced therein.

The present embodiment may be used in dogs, horses, and other animals for clot dissolution or clot prevention. Treatment and maintenance regimens will vary based on the weight of the animal and size of the clot.

I claim:
1. A method of dissolving a feline thrombus comprising:
administering to the feline from 10 to 30 tablets of an enzymatic formula containing nattokinase and an enteric coating;
wherein each tablet comprises nattokinase at 37.5 mg/750 fibrinolytic units.
2. The method of claim 1, wherein each tablet further comprises rutin bioflavonoid at 50 mg.

3. The method of claim 1, wherein each tablet comprises nattokinase at 112.5 mg/2,250 fibrinolytic units.

4. The method of claim 1, wherein the thrombus comprises a feline arterial thromboembolism.

5. The method of claim 3, wherein each tablet further comprises rutin bioflavonoid at 150 mg.

6. The method of claim 1, wherein each tablet further comprises rutin bioflavonoid at 50 mg.

7. The method of claim 6, further comprising administering a second amount of 10 to 30 tablets 12 hours after the initial amount.

8. The method of claim 3, further comprising administering a second amount of 10 to 30 tablets 12 hours after the initial amount.

9. The method of claim 7, wherein orally administering the second amount is continued with 2 tablets daily.

10. The method of claim 7, wherein orally administering the second amount is continued with 4 tablets daily.

11. The method of claim 8, wherein orally administering the second amount is continued with of 6 tablets daily.

12. The method of claim 7, wherein orally administering the second amount is continued with 5 tablets about every 12 hours, wherein each tablet comprises nattokinase at 225 mg/4500 fibrinolytic units, and rutin bioflavonoid at 300 mg.

13. A method of administering a thrombolytic formula to a feline comprising: administering to the feline a formula orally every 12 hours for a treatment duration, the formula comprising 10 to 30 tablets, wherein each tablet comprises (A) nattokinase at 112.5 mg/2250 fibrinolytic units, and rutin bioflavonoid at 150 mg, or (B) nattokinase at 225 mg/4,500 fibrinolytic units, and rutin bioflavonoid at approximately 300 mg.

* * * * *